United States Patent [19]
Eisenberg et al.

[11] Patent Number: 6,010,896
[45] Date of Patent: Jan. 4, 2000

[54] LYOPHILIZED IONIZING RADIATION STERILIZED MICROORGANISMS AS AN ADDITIVE FOR NUTRIENT MEDIA FOR GROWING BACTERIA

[75] Inventors: Eli Eshet Eisenberg, Tel-Aviv, Israel; George L. Evans, Cockeysville, Md.

[73] Assignee: Becton, Dickinson and Company, Franklin Lakes, N.J.

[21] Appl. No.: 07/719,872

[22] Filed: Jun. 24, 1991

[51] Int. Cl.[7] ................ C12N 1/04; C12N 1/12; C12N 1/20; C12N 11/10
[52] U.S. Cl. .......... 435/252.1; 435/243; 435/252.8; 435/253.6; 435/178; 435/801; 435/822; 435/849
[58] Field of Search ............. 435/252.1, 240.22, 435/252.8, 849, 968, 253.6, 243, 178, 801, 822; 424/93

[56] References Cited

U.S. PATENT DOCUMENTS

| | | | |
|---|---|---|---|
| 3,592,740 | 7/1971 | Christensen | 195/96 |
| 4,071,412 | 1/1978 | Eisenberg et al. | 195/102 |
| 4,329,431 | 5/1982 | Youssef | 435/253.6 |
| 4,391,909 | 7/1983 | Lim | 435/178 |
| 4,402,986 | 9/1983 | Sinkoff et al. | 426/41 |
| 4,476,224 | 10/1984 | Adler | 435/253 |
| 4,672,037 | 6/1987 | Daggett et al. | 435/253 |
| 4,879,239 | 11/1989 | Daggett et al. | 435/252.1 |

*Primary Examiner*—David M. Naff
*Assistant Examiner*—Deborah Ware
*Attorney, Agent, or Firm*—Bruce S. Weintraub

[57] ABSTRACT

A media additive for the promotion of the growth of anaerobic and aerobic bacteria is presented. The additive comprises lyophilized microorganisms exposed to ionizing radiation. The microorganisms are *Escherichia coli* ATCC 25922 and *Escherichia coli* ATCC 110303. Such microorganisms are incapable of multiplication, yet retain many of their metabolic pathways, enzymes, and biologically active compounds, permitting them to be utilized by the bacteria to be cultured.

19 Claims, No Drawings

LYOPHILIZED IONIZING RADIATION STERILIZED MICROORGANISMS AS AN ADDITIVE FOR NUTRIENT MEDIA FOR GROWING BACTERIA

BACKGROUND OF INVENTION

The culture of bacteria and other microorganisms is an important technique for diagnostic and biomedical purposes. In standard culture techniques, bacteria are placed in contact with a medium which contains the nutrients necessary for sustaining growth and multiplication, and incubated under appropriate conditions to encourage such growth and multiplication.

However, this procedure is often long and tedious. Additionally, many bacteria cannot be easily cultured. For example, strict anaerobes are sensitive to oxygen and will not grow in its presence. Fastidious bacteria, on the other hand, are unable to metabolize many medium components and require a complex set of nutrients for growth. Thus, culture media must be pre-treated and/or fortified to permit use with specific bacteria.

Researchers have attempted to use additives to improve media for particular applications. For example, U.S. Pat. No. 4,476,224 to Adler discloses that oxygen can be removed from a culture medium (thereby increasing its utility in anaerobic culture) by the addition of sterilized bacterial membrane fragments. Such a product is sold by Oxyrase, Inc. under the name Oxyrase™ Enzyme System. However, the utility of this additive is limited to anaerobic culture.

Similarly, the addition of various nutrients to a culture medium is known in the art. However, this again is limited only to the culture of organisms having those particular nutrition requirements.

There exists a real need for media additives which will promote the growth of a wide array of bacteria, and which are compatible with different media.

Accordingly, it is an object of this invention to present a culture medium additive which is capable of promoting the growth of all types of bacteria, including anaerobic, facultatively anaerobic, and aerobic bacteria, on a variety of media. It is further an object of this invention to present a medium additive capable of promoting the growth of fastidious bacteria, whether strict anaerobes or not.

SUMMARY OF THE INVENTION

The above and related objects are realized by the culture media of this invention. These media are modified by the addition of an additive prepared by subjecting lyophilized microorganisms to ionizing radiation. The resultant material contains an array of nutrients and enzymes which can be utilized by bacteria (as used herein the term "bacteria" shall be inclusive of all microorganisms) for growth.

Key to the preparation of the additive is the use of ionizing radiation. Such treatment renders the microorganisms incapable of multiplication but, it has been found, does not destroy many of the enzymes and biologically active compounds in the microorganisms, permitting them to be utilized by bacteria. Since many of these compounds are heat labile; such additives cannot be obtained by heat sterilization.

The additives can also, optionally, be encapsulated in an encapsulant such as calcium alginate, to permit use in liquid media without attendant turbidity or staining problems.

DETAILED DESCRIPTION OF THE INVENTION

The additives used in the media of this invention promote the growth of aerobic, facultatively anaerobic, and strict anaerobic bacteria, by the use of lyophilized microorganisms exposed to ionizing radiation. Such compositions are rich in active enzyme systems and in both thermolabile and thermostable growth-promoting substances. Key to the additive preparation is the use of ionizing radiation, which confers the following advantages on the system:

1. Since genetic material of living cells is generally more radiosensitive than their enzyme systems, radiation-treated cells lack the ability to multiply (i.e. are sterile), but retain their active metabolic pathways. Such pathways are available for use by bacteria, placed in contact with the cells.
2. Radiation treatment can be performed without raising the product temperature, thus retaining the nutritive value of thermolabile substances.
3. Ionizing radiation, because of its high penetration, permits the treatment of products in their final package, guaranteeing ultimate sterility of preparations, even when prior aseptic steps are involved.

The additives of this invention are produced from radiosensitive microorganisms, which are rich in active metabolic enzyme systems and thermolabile growth promoting substances. The desired effects can be achieved at a low radiation dose, thus minimizing the harmful effects of ionizing radiation on the metabolic systems and nutrients that are to be utilized. While virtually any such microorganisms can be used, the preferred microorganism is *Escherichia coli*.

The additives of this invention improve the growth of anaerobic bacteria primarily by creating anaerobic conditions in the medium due to oxygen consumption by the metabolic pathways of the irradiated cells, and secondarily by the contribution of other enzymes such as catalase and superoxide dismutase, which catalyze the neutralization of toxic products. The growth of fastidious and aerobic bacteria is enhanced due to the presence of heat labile nutrients and active enzyme systems utilized in the metabolic process of these organisms; such enzyme systems and nutrients are generally deficient in ordinary culture media. In fact, the presence of these enzymes counteracts, it has been found, the effects of the oxygen consumption of the metabolic pathways; thus, growth of aerobic bacteria is also enhanced.

The additives can be prepared in free or encapsulated forms, permitting wide discretion in ultimate application.

In preparation of the free form additives, the microorganisms are grown under conditions of active multiplication, (on a liquid or solid medium), harvested, and washed (preferably with distilled water or buffered saline at pH 7.3). The microorganisms are subsequently lyophilized and exposed to ionizing radiation of a sufficient does to achieve sterilization (generally 0.5–1.5 Mrad).

In preparation of the encapsulated additives, the microorganisms are grown and harvested as described above, then encapsulated. A representative procedure for the preparation of microorganisms encapsulated in calcium alginate appears below.

1. The harvested microorganisms are mixed with a sterile solution of sodium alginate;
2. The mixture is subsequently mixed with a sterile aqueous solution of calcium chloride to form a precipitate of entrapped microorganisms in calcium alginate;
3. The encapsulated precipitate is washed in distilled water and then lyophilized; and
4. The ultimate material is sterilized by ionizing radiation.

Regardless of the method used for preparation, the resultant additives can be admixed with virtually any culture medium to obtain a medium capable of promoting growth. The additives are preferably admixed at a concentration of freeze-dried cells equivalent to a starting viable count of about $1 \times 10^7 - 1 \times 10^{13}$ CFU/ml (note: since the microorganisms cannot multiply, the term CFU does not directly apply; hence "equivalent" counts are given).

EXAMPLES

The following examples illustrate certain preferred embodiments of this invention but are not intended to be illustrative of all embodiments.

Example 1

E. coli, ATCC 25922, was subcultured on Trypticase Soy Blood Agar (BBL®) and incubated for 18 h at 35° C. The organism was then suspended in normal saline and adjusted to the turbidity of a 0.5 McFarland standard; 0.1 ml was inoculated into seven culture bottles, each containing 200 ml of Trypticase Soy Broth (BBL®). The inoculated broth was incubated at 37° C. for 10 h with aeration, and subsequently centrifuged to harvest the bacterial cells. The cells were washed with and resuspended in buffered saline, and the washing and centrifuging was repeated. The resultant harvested cells were suspended in buffered saline to a concentration of $8.6 \times 10^{10}$ CFU/ml. The yield was 70 ml of concentrated suspension from 1400 ml of culture media.

The concentrated suspension was dispensed in 1.0 ml aliquots into serum vials, freeze dried and stoppered under a vacuum of about 40 Millitorr. The material was irradiated at room temperature up to a dose of 1 Mrad and stored at 2–8° C. The $D_{10}$ value (the dose needed to reduce the population by $10^1$ CFU, 1 log) was found to be 14.7 Krads. The material irradiated at 1 Mrad was checked for sterility and found to be sterile.

Example 2

The material was prepared as described in Example 1 using E. coli ATCC 11303. The yield was 40 ml of concentrated suspension containing $2.3 \times 10^{10}$ CFU/ml from 1800 ml of culture media. The $D_{10}$ value of the freeze dried organism was 0.76 Mrad. The material irradiated at 1 Mrad was found to be sterile.

Example 3

A concentrated suspension of E. coli 25922 was prepared as described in Example 1 (except that washing of cells was done with distilled water). The yield of harvested cells was 20 ml containing $2.7 \times 10^{11}$ CFU/ml from 1400 ml of culture media. The harvested cells were stored overnight at minus 65° C. After thawing, the cells were mixed at a ratio of 1:2 with a 2% solution of sodium alginate (A-2033 Sigma, medium viscosity) and 1 ml portions were injected into serum bottles containing 5 ml of 0.5% $CaCl_2$. The filaments of encapsulated cells in calcium alginate were cured at room temperature for 1–2 hours. The $CaCl_2$ solution was decanted and the filaments were washed with 5 ml of distilled water, and subsequently freeze-dried and stoppered under a vacuum of 40 Millitorr. The material was irradiated at 1 Mrad and stored at 2–8° C.

Example 4

The preparation from Example 1 was suspended in sterile water equivalent to a concentration of $8 \times 10^{10}$ CFU/ml. Blank paper discs, 0.5 inch diameter (Taxo 31121-BBL®), were moistened with 0.1 ml of this suspension and placed on Group A selective Strep agar (ssA™) containing 5% sheep blood (BBL®), which was previously inoculated with *Streptococcus pyogenes* ATCC 19615. The plates were incubated at 35° C. in air. Enhanced growth and clear beta hemolysis appeared near the disc after 48 h of incubation, while smaller colonies with no zone of hemolysis appeared on control plates. These discs were also tested on Trypticase Soy Agar containing 5% sheep blood and found to produce enhanced growth of *Streptococcus pneumoniae* ATCC 6305.

Discs moistened with 0.1 ml of suspension containing the equivalent of $2.3 \times 10^{10}$ CFU/ml of radiation-sterilized cells of E. coli ATCC 11303 (Example 2) were found to enhance the growth of *B. subtilis* ATCC 6633 (a strict aerobe) when utilized in the above manner.

Example 5

A synthetic medium composed of 0.1M sodium lactate in buffered saline, (pH 7.3) was saturated with air. To 1 ml of this were added the equivalent of $6 \times 10^9$ CFU of irradiated cells of E. coli 25992 as prepared in Example 1. All the oxygen was consumed within 5 minutes at 23° C. and 3 minutes at 35° C. Addition of the same preparation of irradiated cells at a concentration of $10^{10}$ per 1 ml of Columbia broth (BBL®) (saturated with air), removed all of the oxygen within 10 minutes at 23° C. Thus, the irradiated cells will consume air from culture media, to render such media useful for culture of anaerobic bacteria.

Example 6

One ml of encapsulated E. coli 25922 (Example 3) was added to 5 ml of Columbia broth (supplemented with 5 mg/L hemin, 0.5 mg/L vitamin K and 1 g/L $CaCl_2$) and saturated with air. Oxygen was reduced to 0.5% of initial content within 18 minutes at 23° C. The Eh (oxidation-reduction potential) value was reduced to −50 mV and −88 mV after 50 and 150 minutes respectively.

Example 7

Five ml of sterile Columbia broth enriched with 5 mg/L hemin, 0.5 mg/L Vitamin K and 1 g/L $CaCl_2$ were injected into serum vials containing encapsulated E. coli 25922 (Example 3). The vials were incubated in a water bath at 35° C. Methylene blue was added to 2 of these and the color turned from blue to colorless in 30 minutes (indicating the absence of oxygen).

The remaining vials containing the encapsulated microorganisms, control vials containing 5 ml of enriched Columbia broth without encapsulated E. coli, and tubes containing 5 ml of produced Enriched Thioglycollate Medium were each inoculated with about $10^3$ CFU per vial or tube of *Clostridium novyi* ATCC 19402, *Bacteroides melaninogenicus* ATCC 15930, or *Bacteroides fragilis* ATCC 25285, respectively.

To ascertain the effect of direct contact with the encapsulated microorganisms $10^3$ CFU of the 3 test organisms were also added to additional vials containing only the encapsulated microorganisms. After a few minutes of contact, 5 ml of enriched Columbia broth was added. All samples were incubated at 35° C. for 7 days and observed for growth and staining properties.

In those vials that contained encapsulated irradiated E. coli and enriched Columbia broth, all 3 of the test organisms grew well. However, none of them grew in vials that contained only enriched Columbia broth. Growth of *B. melaninogenicus* was accelerated and (growth of *C. novyi* appeared 48 hours earlier in the vials) containing encapsulated *E. coli* compared with Enriched Thioglycollate Medium.

Further, the presence of encapsulated *E. coli* did not interfere with the observations on gram-stained samples taken from those vials.

It is apparent that many modifications and variations of this invention as hereinabove set forth may be made without departing from the spirit and scope hereof. The specific embodiments described are given by way of example only and the invention is limited only by the terms of the appended claims.

What is claimed is:

1. A nutrient media for growing bacteria, wherein the improvement comprises including in the media an effective amount of an additive comprising lyophilized, ionizing radiation-sterilized microorganisms to enhance bacterial growth.

2. The media of claim 1 wherein the microorganisms are *Escherichia coli*.

3. The media of claim 2 wherein the microorganisms are selected from the group consisting of *Escherichia coli* ATCC 25922 and *Escherichia coli* ATCC 11303.

4. The media of claim 1 wherein the additive is present in an equivalent concentration of about $1 \times 10^7$ to about $1 \times 10^{13}$ CFU/ml.

5. The media of claim 1 wherein the microorganisms are in free form.

6. The media of claim 1 wherein the microorganisms are in encapsulated form.

7. The media of claim 6 wherein the microorganisms are encapsulated in calcium alginate.

8. A method for preparing a nutrient media additive for enhancing the growth of bacteria, which method comprises:

(i) growing microorganisms under conditions of active multiplication;

(ii) harvesting and washing the microorganisms;

(iii) lyophylizing the microorganisms; and (iv) exposing said lyophilized microorganisms to ionizing radiation of a sufficient dose to obtain a sterile material.

9. The method of claim 8 wherein the microorganisms are *Escherichia coli*.

10. The method of claim 9 wherein the microorganisms are selected from the group consisting of *Escherichia coli* ATCC 25922 and *Escherichia coli* ATCC 11303.

11. The method of claim 8 wherein the microorganisms are grown on solid media.

12. The method of claim 8 wherein the microorganisms are grown in liquid media.

13. The method of claim 8 wherein the harvested microorganisms are washed with distilled water.

14. The method of claim 8 wherein the harvested microorganisms are washed in pH 7.3 buffered saline.

15. A method for preparing a nutrient media additive for enhancing the growth of bacteria, which method comprises:

(i) growing microorganisms under conditions of active multiplication;

(ii) harvesting and washing the microorganisms;

(iii) suspending the microorganisms in a sterile solution of sodium alginate;

(iv) adding to the solution a sterile solution of calcium chloride of a sufficient concentration to form a precipitate of microorganisms entrapped in calcium alginate;

(v) washing the precipitate with distilled water;

(vi) lyophylizing the precipitate; and (vii) exposing said lyophilized precipitate to ionizing radiation of a sufficient dose to obtain a sterile material.

16. The method of claim 15 wherein the microorganisms are *Escherichia coli*.

17. The method of claim 16 wherein the microorganisms are selected from the group consisting of *Escherichia coli* ATCC 25922 and *Escherichia coli* ATCC 11303.

18. The method of claim 15 wherein the microorganisms are grown on solid media.

19. The method of claim 15 wherein the microorganisms are grown in liquid media.

* * * * *